United States Patent [19]

Makino et al.

[11] Patent Number: 5,058,596
[45] Date of Patent: Oct. 22, 1991

[54] OPHTHALMOLOGICAL MEASUREMENT METHOD AND APPARATUS

[75] Inventors: Misao Makino, Hachiouji; Kiyoshi Hashimoto; Toshiaki Sugita, both of Hino, all of Japan

[73] Assignee: Kowa Company Ltd., Japan

[21] Appl. No.: 507,355

[22] Filed: Apr. 9, 1990

[30] Foreign Application Priority Data

Apr. 10, 1989 [JP] Japan ................................ 1-87858

[51] Int. Cl.$^5$ ........................... A61B 3/10; A61B 3/14
[52] U.S. Cl. .................................... 128/665; 128/691; 128/745; 351/221
[58] Field of Search ............... 128/665, 745, 395, 691; 606/2, 3, 4; 356/387; 351/221, 206, 211

[56] References Cited

U.S. PATENT DOCUMENTS

| 4,346,991 | 8/1982 | Gardner et al. | 356/28.5 |
| 4,743,107 | 5/1988 | Aizu et al. | 351/221 |
| 4,848,897 | 7/1989 | Aizu et al. | 351/221 |

Primary Examiner—Ruth S. Smith
Assistant Examiner—Kevin Pontius
Attorney, Agent, or Firm—Bruce L. Adams; Van C. Wilks

[57] ABSTRACT

In an ophthalmological measurement method and apparatus, a laser beam of predetermined diameter is projected to the eye fundus and movement of a speckle pattern formed by light scattered by blood cells in blood vessel is detected by a photosensor as fluctuation in speckle light intensity to produce a speckle signal. The speckle light intensity will fluctuate more rapidly with a smaller output from the photosensor when cell velocities are high, while a low cell travel speed will decrease the lowering of the output therefrom. The speckle signal is then processed to derive therefrom its center of gravity, which is taken as a center of a blood vessel to identify the blood vessel. This enables the blood vessel parts to be identified with high accuracy and to be tracked automatically.

15 Claims, 7 Drawing Sheets

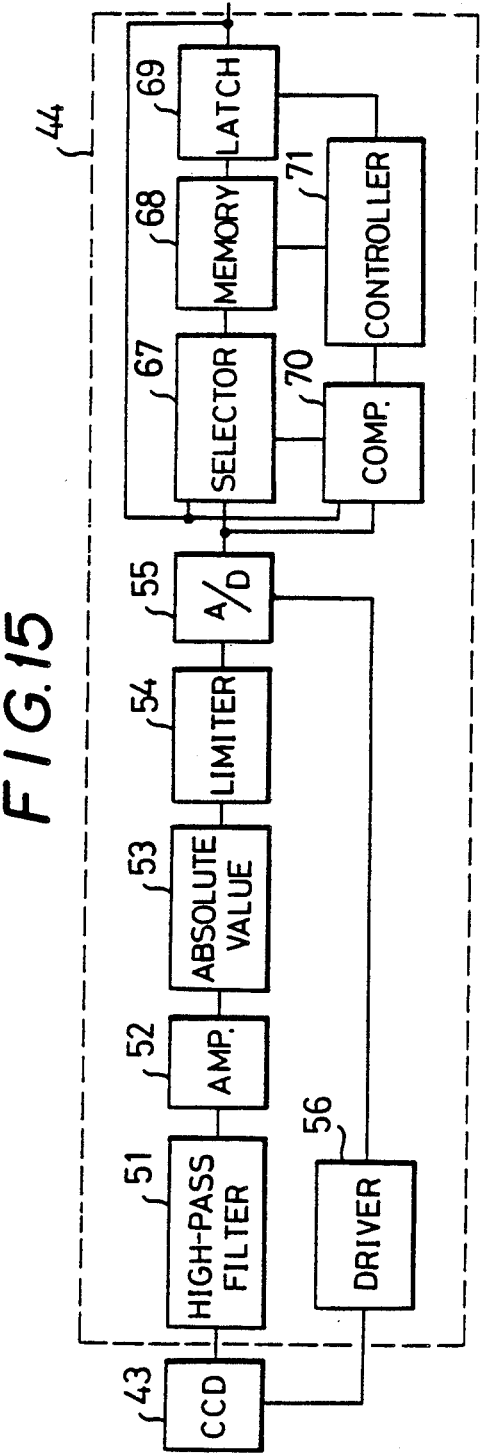
F I G. 15
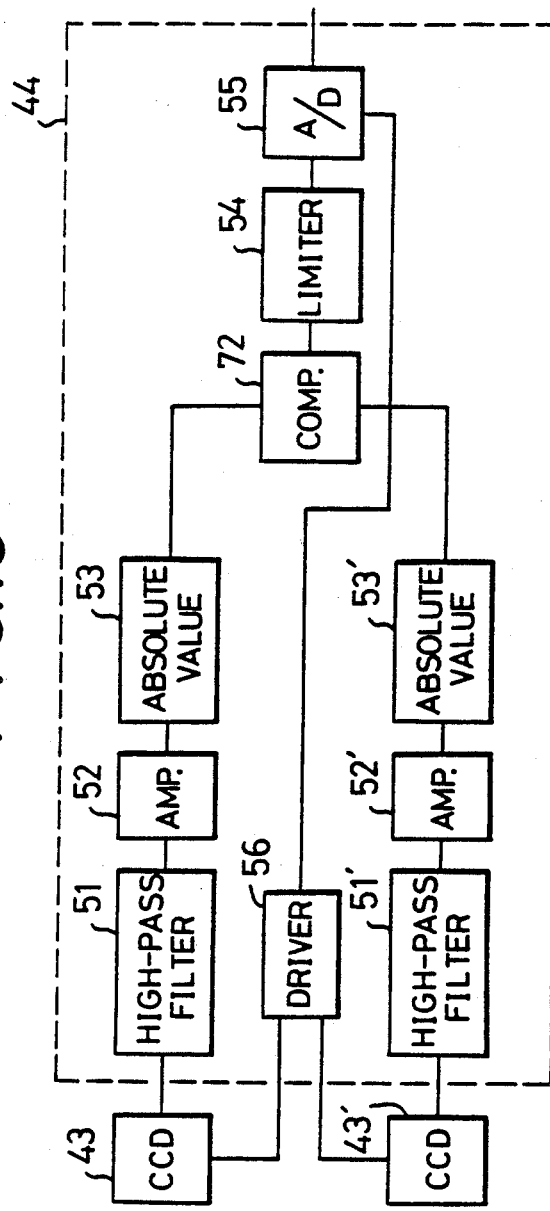
F I G. 16

OPHTHALMOLOGICAL MEASUREMENT METHOD AND APPARATUS

BACKGROUND OF THE INVENTION

1. Field of the Invention

This invention relates to an ophthalmological measurement method and apparatus, and more particularly to an ophthalmological measurement method and apparatus in which the eye fundus is illuminated by a laser beam having a predetermined diameter and motion of a laser speckle pattern formed by laser light scattered and reflected from the eye fundus is detected at an observation point as fluctuations in the speckle light intensity to produce a speckle signal which is evaluated for ophthalmological measurement.

2. Description of the Prior Art

Various conventional methods are used for ophthalmological measurement comprising illuminating the eye fundus with a laser beam, detecting the light scattered by the eye fundus and analyzing and evaluating this light. There are for example laser Doppler methods for measuring blood flow in retinal and other tissue described in "Investigative Ophthalmology," vol. 11 No. 11, page 936 (November 1972) and "Science," vol. 186 (November 1974) page 830, and in Japanese Unexamined Patent Publication Nos. 55-75668, 55-75669, 55-75670, 52-142885 (corresponding to GB 13132/76 and U.S. Pat. No. 4,166,695), 56-125033 (corresponding to GB 79/37799), 58-118730 (corresponding to U.S. Pat. No. 4,402,601) and U.S. Pat. No. 4,142,796. However, these laser Doppler methods involve the use of a high precision optical system, are complicated to use and provide results which lack repeatability and reliability, all of which make practical application difficult.

It is, on the other hand, known that when a laser beam strikes an object which causes diffusion or scattering of the beam, the light scattering from the object gives rise to a speckle pattern caused by interference between reflected rays of the coherent light. The laser speckle method utilizes this to evaluate the state of tissues in the eye fundus. There are for example the methods described in Japanese Unexamined Patent Publication Nos. 62-275431 (U.S. Pat. No. 4,734,107 and EPC 234869), 63-238843 (EPC 284248) and 63-242220 (EPC 285314).

These publications describe the use of a detecting aperture to extract time-base fluctuations in the intensity of speckles formed at an optical Fourier Transform plane with respect to the eye fundus, or at the Fraunhofer refraction plane, or at an image plane (or a magnified image plane) that is conjugate with respect to the eye fundus, and the blood flow state is determined by an evaluation of the speckle signal thus obtained.

A major obstacle to the clinical application of the above systems has been their susceptibility to the effects of movements, such as movement of the subject's eye, vibration and the like. This frequently causes unwanted movement of speckle patterns on the detection plane, thus throwing the detecting aperture and laser beam out of alignment during measurement. One way to overcome this is described in the laser-Doppler method of Japanese Patent Publication No. 56-125033. This involves the mechanical scanning the eye fundus image on the detection plane and using differences between the light reflectance of the walls of a blood vessel and that of other areas of tissue to distinguish blood vessels, and correcting for positional deviation. A drawback of this method is that it requires a mechanism for the mechanical scanning of the eye fundus image, which makes the apparatus too large and complex to be practical.

Another method, described in Applied Optics, Vol. 27, No. 6, page 1113 (March 15, 1988) and in Japanese Patent Publication No. 63-288133 (U.S. Pat. No. 14,994), shows the feasibility of an image scanning arrangement which allows blood vessels to be distinguished and tracked automatically. However, the method is based on the wavelength dependency of reflected light and relies for its implementation on a plurality of laser beams of different wavelengths which are projected in sequence. Again, this makes the apparatus complex, impractical and costly. A further drawback is that when corneal reflection is used to detect eye movement, the detection precision is not high enough for the purposes of correcting for movement by the blood vessel.

Conventional tracking methods involving the detection of eye movement include one in which the corneal surface is illuminated by a laser beam and movement of the reflected light is used to detect and track such eye movement, while another method uses differences between two images of the eye fundus obtained by TV camera or other such imaging means.

However, such methods involve detection of eye surface movement and are only able to provide a low level of intraocular tracking precision. Moreover, eye fundus images obtained via a TV camera usually suffer from a poor S/N ratio owing to the amount of light being insufficient for the task, and the apparatus required to detect movement based on differences between two images is large and complex.

SUMMARY OF THE INVENTION

It is therefore an object of the invention to provided an improved ophthalmological measurement method and apparatus employing the laser speckle phenomenon which is simple and straightforward in construction and is able to detect eye movement and automatically track the movement in the eye fundus with good accuracy.

The invention provides an ophthalmological measurement method and apparatus in which the eye fundus is illuminated by a laser beam having a predetermined diameter and motion of a laser speckle pattern formed by laser light scattered and reflected from the eye fundus is detected at an observation point as fluctuations in the speckle light intensity to produce a speckle signal which is evaluated for ophthalmological measurement. In this arrangement the speckle signal is then evaluated to derive its center of gravity, which is taken as a central position of a blood vessel in the eye fundus to identify a blood vessel part of the eye fundus.

Any movement of the identified blood vessel part of the eye fundus is detected, and the position of the region illuminated by the laser beam and the position of the observation point are adjusted by an amount corresponding to the amount of blood vessel movement to track the blood vessel part automatically. In such an arrangement, the laser beam of predetermined diameter is projected into the eye fundus by a laser beam projector and the movement of a speckle pattern formed by diffused light scattered by blood cells within the eye tissue passes through a light receiving system and is detected by a photosensor as fluctuation in speckle light intensity. The speckle signal mirrors the travel speed of the blood cells in the eye tissues. The size of speckles on the photosensor and the scanning speed of the photosensor are optimally set. The speckle light intensity will fluctuate more rapidly when cell velocities are high, and the averaging effect of the photosensor's storage time will result in a smaller output. Conversely, a low cell travel speed will decrease the lowering of the output from the photosensor. The speckle signal is then processed to derive therefrom its center of gravity, which is determined as a center of a blood vessel to identify the blood vessel. This enables the blood vessel parts to be identified with high accuracy. Movable mirrors are driven by an amount corresponding to shifts in the position of the blood vessel caused, for example, by eye movement, so that the position of the region illuminated by the laser beam and the observation position are controlled to automatically track the blood vessel, thus enabling a precise automatic blood vessel tracking with a simplified structure.

BRIEF DESCRIPTION OF THE DRAWINGS

The objects and features of the present invention will become more apparent from a consideration of the following detailed description taken in conjunction with the accompanying drawings in which:

FIGS. 15 and 16 are schematic views of a signal processor;

DETAILED DESCRIPTION OF THE PREFERRED EMBODIMENTS

Figure 1:
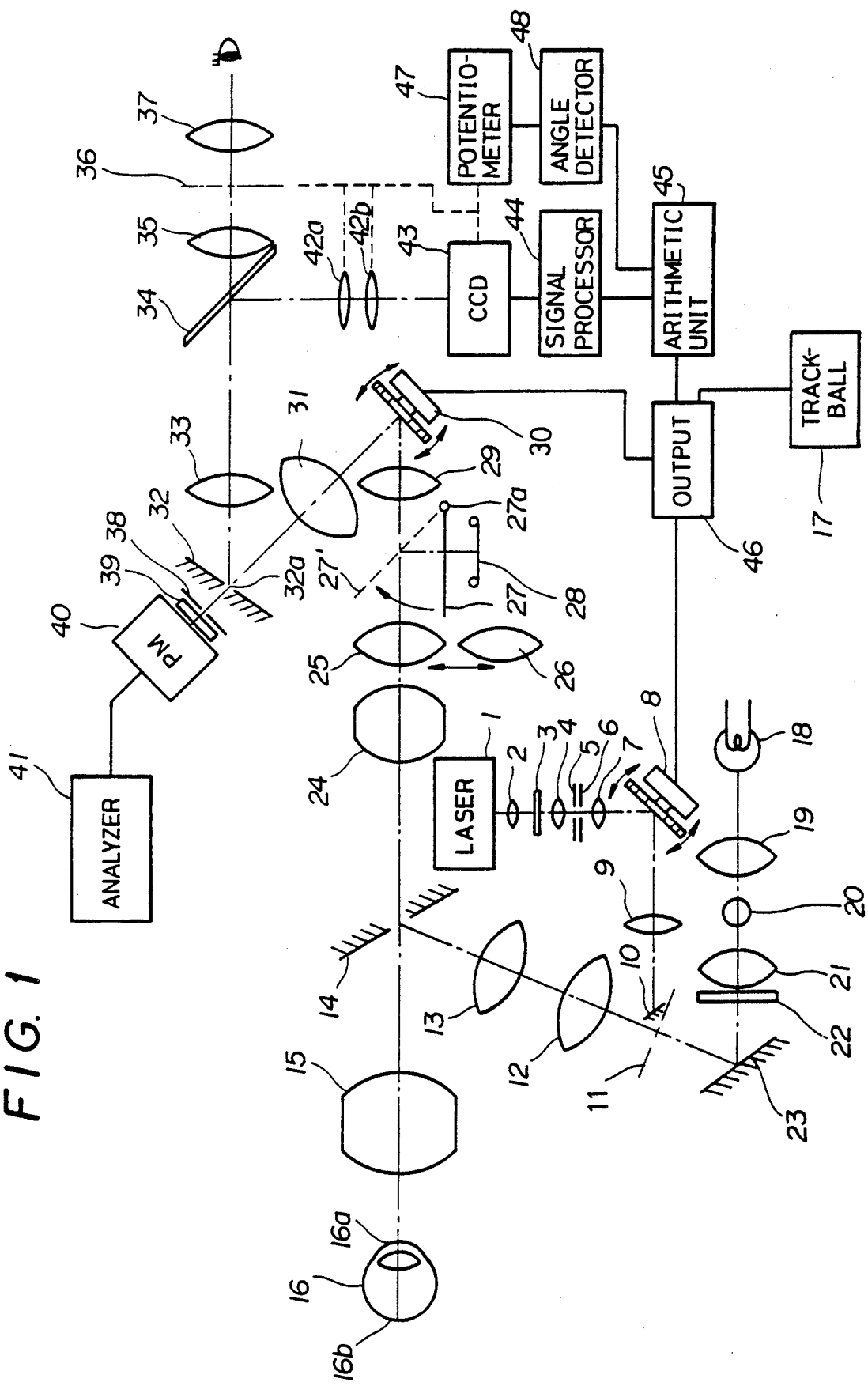
FIG. 1 is a diagram showing the structure of a first embodiment of an apparatus according to the present invention.

The invention will now be described in detail with reference to embodiments shown in the drawings.

The invention is particularly used for an ophthalmological measurement apparatus in which the eye fundus is illuminated by a laser beam having a prescribed diameter and motion of a laser speckle pattern formed by laser light scattered and reflected from the eye fundus is detected at an observation point as fluctuations in the speckle light intensity to produce a speckle signal which is evaluated to measure a blood flow state in tissues in the eye fundus. Therefore, the embodiments described below are those which are applied to the ophthalmological measurement apparatus including a basic optical arrangement of an eye fundus camera to measure the blood flow state in the eye fundus tissue. The invention is, however, not limited to such embodiments but will be applied to another type of ophthalmological apparatus.

With reference to FIG. 1, a laser beam from a redlight He-Ne (wavelength: 632.8 nm) laser light source 1, for example, passes through a condenser lens 2 and a light quantity adjustment filter 3 for adjusting the beam intensity, and is then collimated by a collimator lens 4. Two apertures 5 and 6 are provided within the path of the beam for selectively adjusting the size and shape of the region of an eye fundus 16b of a subject's eye 16 being illuminated by the laser beam.

Figure 2:
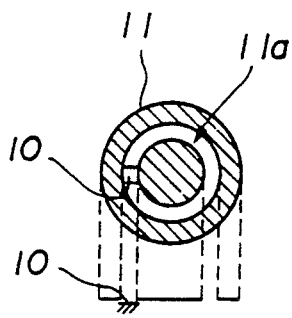
FIG. 2 is a diagram for explaining the structure of a ring slit.

The laser beam passes through a condenser lens 9 and is reflected by a mirror 10 provided in a transparent portion of an annular aperture 11a formed in a ring slit 11 arranged in an eye fundus camera illuminating projector, as shown in FIG. 2 (in which the nontransparent portion is indicated by shading). Such an arrangement enables the laser beam to direct along the same optical path to the eye fundus as that followed by the beam of light projected into the eye fundus to provide illumination for photography and observation. The laser beam thus passes through relay lenses 12 and 13, is reflected by a ring mirror 14 and, via an objective lens 15, passes via the cornea 16a of the eye under examination 16 to the eye fundus 16b where the blood vessel of interest is irradiated with the laser beam for measurement and tracking.

A swingable mirror 8 is provided in the optical laser beam illumination system to deflect the laser beam spot in the eye fundus 16b. Prior to the start of measurement, this deflection is performed via an output section 46 using a means such as a trackball 17. The swingable mirror 8 can be controlled by an ordinary method such as a coagulator arrangement which allows independent control of the angle of mirror deflection in the x and y directions relative to the optical axis.

To minimize the discrepancy that has to be corrected arising from differences in laser beam deflection angles in the x and y directions, the angle at which the laser beam is reflected by the swingable mirror 8 is made as small as space will permit. The swingable mirror 8 is disposed at a position that is substantially a conjugate of the cornea 16a or pupil of the eye. This assures that the laser beam can be moved over the eye fundus without any major change in the position of beam incidence on the cornea.

The laser beam is provided on the same optical path as the photography and observation light beam. This arrangement is highly convenient since it enables the location within the eye fundus 16b at which the laser beam is being projected by the swingable mirror 8 to be brought within the field of view for photography or observation by using mechanisms for swinging and tilting the eye fundus camera vertically and horizontally and the eye fixation means.

This measurement and tracking region is also illuminated by an illuminating projector of the fundus camera to facilitate observation. The system for providing the illumination for observation is constituted of an observation light source 18, a condenser lens 19, a condenser lens 21, a filter 22 and a mirror 23 disposed on the same light path as a photographic light source 20.

Figure 3:
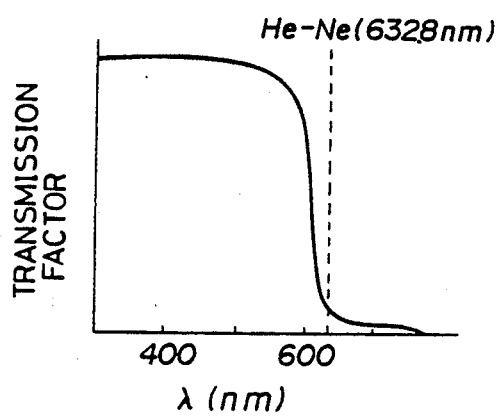
FIG. 3 is a characteristic curve showing the characteristics of a filter.

The filter 22 disposed between the condenser lens 21 and the mirror 23 is a wavelength separation filter having the type of characteristics shown in FIG. 3 to filter out red components from the observation and photographic light. A filter is selected that has spectral characteristics appropriate to the wavelength of the laser beam source that is employed.

Speckle light produced by the scattering of the laser beam in the eye fundus and reflected observation and photographic light passes through the objective lens 15, the ring mirror 14, a focusing lens 24, an imaging lens 25 or 26 and a relay lens 29, is reflected by a movable mirror 30 and passes through a relay lens 31 and is thereby formed into an image at a ring mirror 32. The light reflected by the ring mirror 32 passes through a relay lens 33 and is divided by a wavelength separation mirror 34. Cylindrical imaging lenses 42a and 42b form speckle light reflected by the wavelength separation mirror 34 into an image on a scanning type sensor CCD 43. The wavelength separation mirror 34 is set at an angle of about 45 degrees relative to the optical axis and as the wavelength separation mirror 34 has the same kind of spectral characteristics as wavelength separation filter 22, shown in FIG. 3, it reflects most of the speckle light produced by the red He-Ne laser beam.

Light that is transmitted by the wavelength separation mirror 34 passes through an imaging lens 35 and forms an image at a reticle 36. The examiner can view this image through an eyepiece 37. The eyepiece 37 can be adjusted to compensate for individual differences in visual acuity; the reticle 36 is used as a reference for such adjustments.

Figure 4:
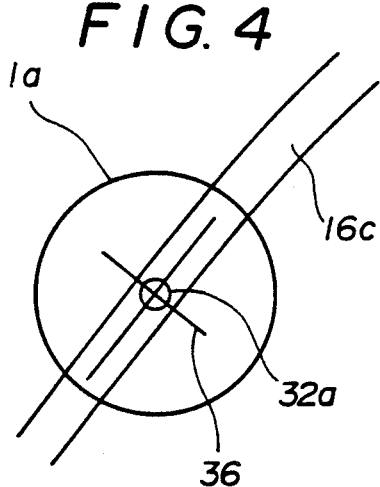
FIGS. 4 and 5 show observed images of the eye fundus.
Figure 5:
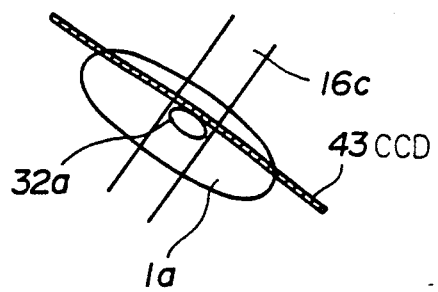

With reference to FIG. 4, the lines of the reticle 36 which intersect at right-angles can be differentiated, and the intersecting portion coincides with the center of an aperture 32a in the ring mirror 32. The reticle 36 can be rotated about the intersecting portion. Rotation of the reticle 36 to align it with a blood vessel 16c, as shown in FIG. 4, produces a synchronous rotation of the cylindrical imaging lenses 42a and 42b and the CCD 43, automatically orienting the CCD 43 perpendicularly to the image of the blood vessel. FIG. 5 illustrates the eye fundus image that will thus be formed on the face of the CCD 43. In the drawing, la denotes the area illuminated by the laser beam.

In view of factors relating to the diameter of speckles, the boiling motion of the speckle pattern and the sensitivity of the CCD 43, the cylindrical imaging lenses 42a and 42b are set so that the image of the eye fundus is formed on the CCD 43 with a lower magnification when it is in a direction parallel to the blood vessel 16c than when it is orthogonal to the blood vessel. As shown in FIG. 5, CCD 43 is provided at a position at which the image of the aperture 32a of the ring mirror 32 does not cross the face of the CCD 43, and the CCD 43 is arranged perpendicularly to the blood vessel 16c of interest.

For photography purposes a swingable mirror 27 is pivoted about a point 27a in the direction indicated by the arrow to raise it to a position 27', whereby the observation and photographic light including speckle light from the eye fundus that is reflected by the swingable mirror 27 and forms an image which is photographed on photographic film 28. Thus, the system can be used for observation and photography of the eye fundus like an ordinary fundus camera. The ability to observe and photograph the eye fundus when it is being illuminated by the laser beam is desirable, as it enables the point of measurement to be directly confirmed and filmed.

In a system for receiving speckle light from the eye fundus and reflected light for observation and photography, light passing through the aperture 32a of the ring mirror 32 forms an image of the eye fundus 16b at a pinhole aperture 38. The light from the pinhole aperture 38 passes through an interference filter 39 and, when measurement is started, is received by a photomultiplier 40 which outputs a speckle signal to an analysis section 41. The interference filter 39 blocks light having a wavelength other than the 632.8 nm red light produced by the He-Ne laser.

The swingable mirror 30 is provided in the system for receiving speckle light from the eye fundus and light for observation and photography for positional correction purposes so that the image of the blood vessel in the eye fundus 16b is formed at the pinhole aperture 38 after passing through the ring mirror 32. Prior to the start of measurement, this adjustment is effected via the output section 46 using a means such as a trackball 17.

As described above, the trackball 17 is also used for operating the swingable mirror 8 prior to the measurement. A switch or other such means may be provided to switch trackball control between the swingable mirror 8 and the swingable mirror 30. The swingable mirror 30 can be controlled by any ordinary means which allows independent control of the angle of mirror deflection in the x and y directions relative to the optical axis. This applies also to the swingable mirror 8.

To minimize the discrepancy that has to be corrected arising from differences in laser beam deflection angles in the x and y directions, the angle at which the laser beam is reflected by the swingable mirror 30 is made as small as space will permit.

By locating the swingable mirror 30 at a position that is substantially a conjugate of the cornea 16a or pupil of the eye, the mirror 30 can be deflected to move the eye fundus 16b image at the pinhole aperture 38 without the beam being blocked by the pupil or other portion of the eye.

In the light receiving system the imaging lens 25 is a wide angle type, wide enough to provide a view which allows all of the image of the eye fundus 16b to be checked. The imaging lens 26 is a narrow angle type with a high magnification factor which provides a magnified image to make it easy that the blood vessel image in the area illuminated by the laser beam is aligned with the pinhole aperture 38.

The imaging lenses 25 and 26 are arranged so that they can be switched instantaneously without moving the optical axis. This variable power lens arrangement facilitates accurate beam alignment with the required measurement position.

The diameter of the ring mirror 32 is just large enough to allow the passage of the light beam from the blood vessel 16c of interest, and the ring mirror 32 is located at a position that is substantially a conjugate of the eye fundus 16b. This assures that the examiner can align the system accurately by manipulating the image of the blood vessel of interest so that the image overlays the aperture of the ring mirror 32. FIG. 4 shows the image that this will produce. As the wavelength separation mirror 34 passes a small amount of speckle light, it is possible for the examiner to confirm the position of the illuminated area 1a.

When measurement is started, speckle light is received by the CCD 43 which outputs a signal to a signal processor 44. The signal processor 44 produces a blood vessel discrimination signal which is converted to a digital signal and output. If the blood vessel has moved owing to movement of the eyeball, for example, the amount of this movement is detected from the digital blood vessel discrimination signal by an arithmetic unit 45 which computes a correction amount by which the blood vessel as detected is to be moved back to an initial position. The computation result is output to the output section 46 which uses feedback correction to control the swingable mirror 30 and swingable mirror 8 so that the image of the eye fundus is constantly maintained at the same position at the pinhole aperture 38 and the laser beam continues to illuminate the same region in the eye fundus 16b.

The arithmetic unit 45 further serves to distinguish the blood vessel parts on the basis of the blood vessel discrimination signal and to calculate the blood vessel diameter. After calculation the results are output to the output section 46, which then displays the blood vessel diameter on a display.

Observation and photography light (other than red component light) together with the small amount of speckle light is transmitted by the wavelength separation mirror 34 and forms an image of the eye fundus at the reticle 36 also during the measurement process, and can therefore be observed by the examiner. The ability to thus observe the eye fundus during blood flow measurement is highly effective for preventing errors, as it enables any deviation from the area of interest to be observed.

Figure 6:
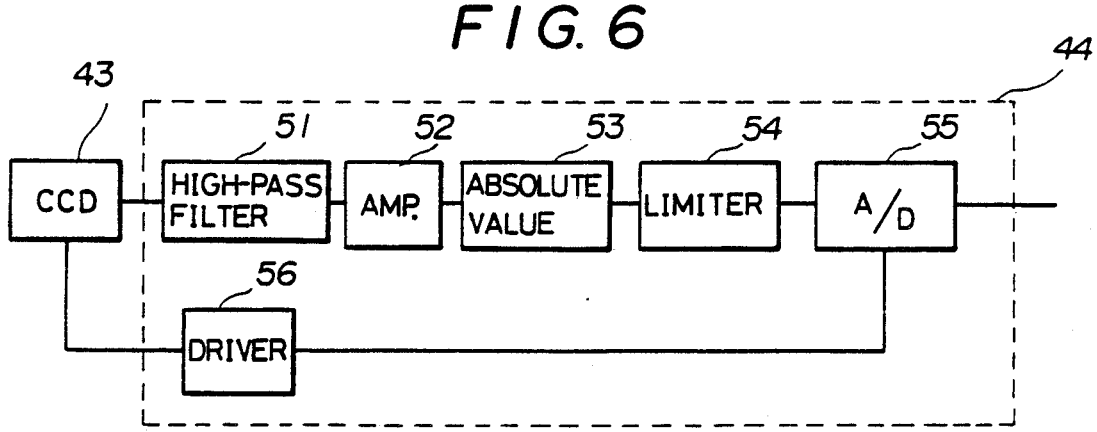
FIG. 6 is a block diagram of a signal processor used in the embodiment.

The electrical system from the signal processor 44 onwards will now be described. FIG. 6 is a schematic diagram of the signal processor. With reference to the drawing, the signal processor 44 is constituted of a drive circuit 56, a high-pass filter 51, an amplifier 52, an absolute value circuit 53, an amplifier with limiter 54 and an A/D converter 55. Drive pulses generated by the drive circuit 56 are input to a 1,024-pixel linear CCD 43. The CCD 43 converts to the speckle light to obtain a speckle signal which is passed through the high-pass filter 51 to extract just the high frequency components. This high frequency component signal is then amplified by the amplifier 52 and passed through the absolute value circuit 53 to obtain an absolute value.

Figure 7:
FIG. 7 shows the waveform of the signal output of an absolute value circuit.
Figure 8:
FIG. 8 shows the waveform of the signal output of amplifier with limiter of the embodiment.

The output signal thus obtained from the absolute value circuit 53 is illustrated in FIG. 7. The signal waveform shown is only that obtained from the central area of the CCD, not the whole; this also applies to FIGS. 8, 12 and 13. The signal is then input to the amplifier with limiter 54 to extract a blood vessel discrimination signal by selectively amplifying the required portions such as the portion A shown between the dotted lines in FIG. 7, the other, unnecessary parts being cut off by the limiter. The signal output by the amplifier 54 is illustrated in FIG. 8. The blood vessel discrimination signal thus obtained is converted to digital form by the A/D converter 55 and input to the arithmetic unit 45.

Figure 9:
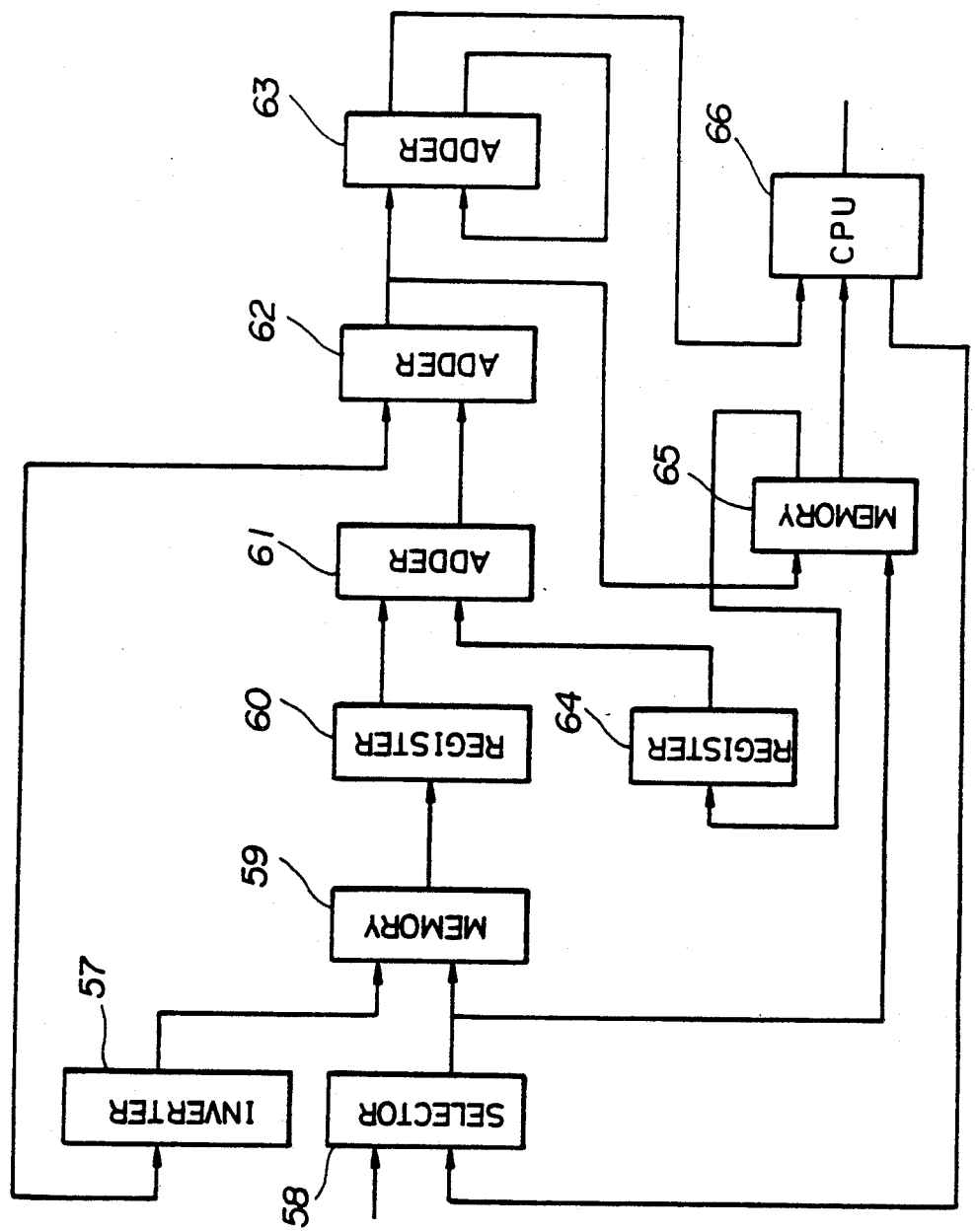
FIG. 9 is a block diagram showing an arrangement of an arithmetic unit.

FIG. 9 shows a block diagram of the arithmetic unit 45, which comprises an inverter 57, a selector 58, a memory 59, a register 60, adders 61 to 63, a register 64, a memory 65 and a CPU 66. The input data are stored in the memory 59 via the inverter 57. The memory 59 is provided with a plurality of banks the number of which corresponds to the number of integrations. If there are thus k integrations, k banks are provided. The memories 9 and 65 read the data in synchronism with the first half of clocks and write them in synchronism with the other half thereof. The data read out from the memory 59 are data which are written prior to k banks, that is, prior to one cycle and which are loaded into the register 60.

The register 60 initiates to operate (k−1) later than the register 64. The register 64 is loaded with the integrated values up to one bank before the memory 65, i.e., k-integration values $Si-1+Si-2+Si-3+...Si-k$. The adder 61 adds the values from the registers 60 and 64 and further adds one. The data from the register 60 are inverted data $Si-k$, so that the further addition of one means the subtraction of the value in the register 60 from the value in the register 64.

That is, the adder 61 forms a value $Si-1+Si-2+Si-3+...Si-(k-1)$. The adder 62 then adds a value Si to form a new integrated value $Si+Si-1+Si-2+Si-3+...Si-(k-1)$, which is stored into the memory 65. The adder 63 further adds one bank data to the output of the adder 62 to provide a sum total corresponding to the integration of one bank pixels.

The sum total formed by the adder 63 and integrated value stored in the memory 65 are input to the CPU 66, which successively adds them until the added value reaches the half of the sum total in the adder 63. The sum total of the adder 63 is equal to the summation of the values in the memory 65, so that when the addition is carried out up to the half sum total the address of the memory 65 is equal to the address of the center of gravity in the memory 65. Since the blood vessel image is substantially symmetrical, the center of gravity can be taken as the center of the blood vessel.

The memory 65 stores the integrated value, which is less affected by noise and thus stable if no movement takes place in the blood vessel. Therefore, the comparison of positions of the center of gravity obtained per one bank enables any movement of the blood vessel to be recognized. Thus, the comparison of the current center of gravity with the initial position makes it possible to determine the amount of movement from the initial position. If this amount of movement from the initial position has been determined, an amount of correction is calculated to bring the blood vessel back to the initial position.

In the output section 46 a pulse motor is driven by an amount that is in accordance with the correction amount output by the arithmetic unit 45, controlling the swingable mirrors 8 and 30 linked to the pulse motor. For automatic tracking, the swingable mirror 8 is driven to move the laser beam to the center of the blood vessel concerned. Likewise, the swingable mirror 30 is driven to implement automatic tracking by moving the speckle pattern observation point to the center of the blood vessel concerned.

When information is being obtained from a blood vessel in the eye fundus, in some cases there will be differences between measured values obtained from the center and the edges of a blood vessel. Central position correction is used to eliminate variance caused by such a difference.

Figure 10:
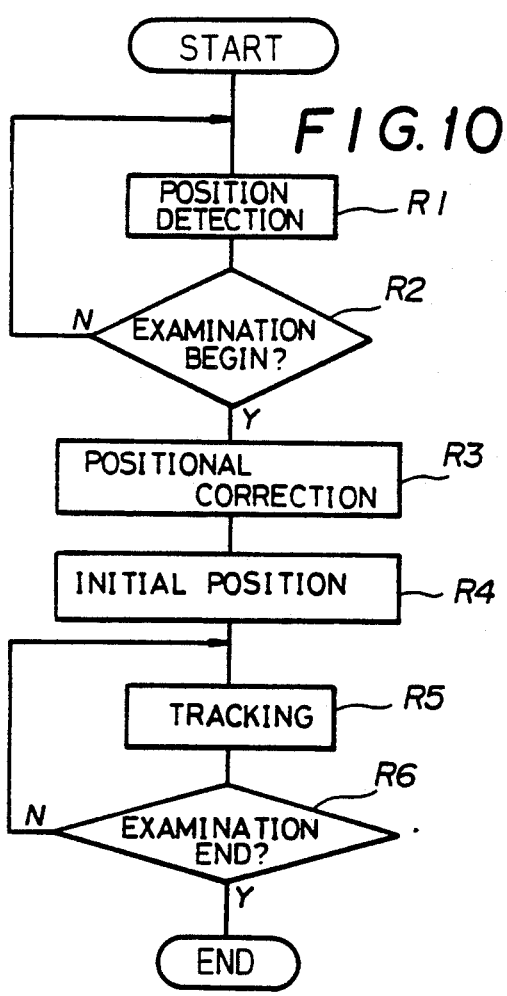
FIG. 10 is a flow chart of the control process for central position correction.

FIG. 10 is a flow chart illustrating the central position correction procedure. Step R1 is for detecting the position of the blood vessel, and in step R2 the position of the blood vessel is detected continuously until the examination is begun. In step R3 the central position of the blood vessel is obtained from the most recent blood vessel position information immediately following the start of examination, the degree of discrepancy between this position and the central position of the CCD 43 is obtained and a correction applied to eliminate any positional discrepancy between the blood vessel center and the CCD center. In step R4 the initial position of the blood vessel is set so that the blood vessel center coincides with the CCD center. In accordance with the initial position set in step R4, in step R5 positional correction is applied constantly to ensure that the center of the blood vessel coincides with the central position of the CCD 43, and this continues until examination is terminated in step R6. With this method, even if the system alignment by the examiner is off-center of the blood vessel, it will still be possible to examine the blood vessel center immediately following the start of the examination.

As described above, as the system is arranged so that when the reticle 36 is rotated relative to the optical axis the CCD 43 also rotates relative to the optical axis, the CCD can be set perpendicularly to the blood vessel. A potentiometer 47 is provided for detecting the angle of rotation of the CCD. An angle detection section 48 applies 8-bit A/D conversion to the output of the potentiometer 47 to obtain angle data, which is input to the arithmetic unit 45 to determine the rotation angle of the CCD. The arithmetic unit 45 calculates and outputs correction amounts to be applied in the x and y directions to correct for movement of the blood vessel.

Figure 11A:
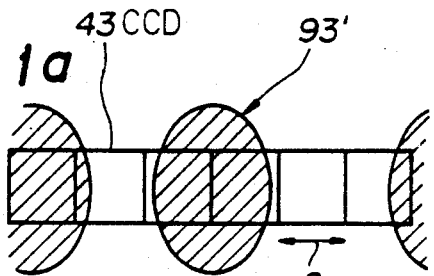
FIGS. 11a to 11f are diagrams showing the relationship between speckle size and CCD pixel size, and output signals.
Figure 11C:
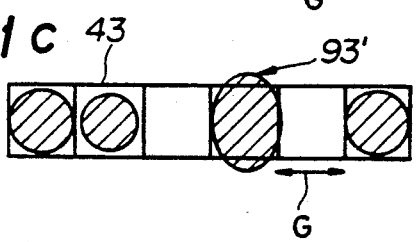
Figure 11E:
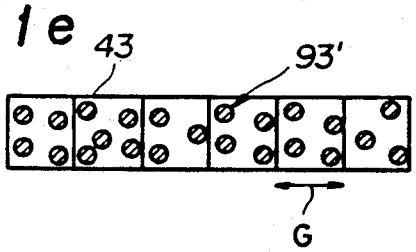
Figure 11B:
Figure 11D:
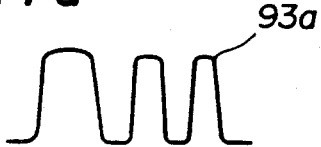
Figure 11F:

It will not be possible to obtain a good speckle signal if there is a large discrepancy between the size of speckle images on the CCD 43 and the size of the CCD's pixels. As shown in FIG. 11a, speckles 93' which are larger than one of the pixels G of the CCD 43 will reduce the amount of incident light on the pixels, making it impossible to obtain a sufficiently strong speckle signal. FIG. 11b shows the type of speckle signal 93a that will result in such a case. On the other hand, speckles 93' which are small compared to the pixels G of the CCD 43, as shown in FIG. 11e, the amount of incident light on the pixels will be averaged out, producing the kind of speckle signal 93a shown in FIG. 11f which lacks contrast. Speckles which are more or less the same size as the pixels as shown in FIG. 11c will produce a good speckle signal such as the signal 93a shown in FIG. 11d.

Figure 12A:
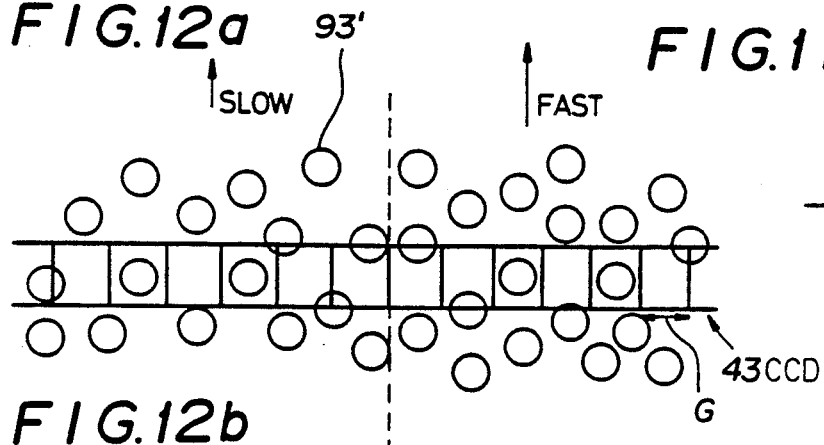
FIGS. 12a and 12b are graphs showing speckle pattern travel speed and the waveform of a CCD output signal.
Figure 12B:
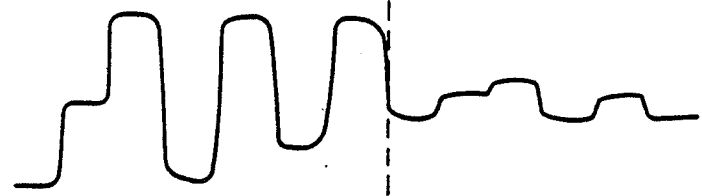

A method of using speckle signals as a basis for discriminating objects traveling at different speeds will now be described. Speckles which have a boiling motion require a complex explanation, so for the sake of simplicity the method will be explained in terms of translational motion. The left half of FIG. 12a depicts blood cells in tissues in the vicinity of blood vessel which have a low travel speed, so the speckles 93' also show a low travel speed. The right half of the drawing depicts blood cells with a high travel speed such as the blood cells in a blood vessel, and which therefore give rise to speckles with a high travel speed. FIG. 12b shows the waveform of the corresponding signals output by a photosensor (i.e. a CCD). If the speed of the speckle pattern is higher than the scanning speed of a scanning sensor, large numbers of dark and light parts of speckles 93' will pass through the light receiving part of the CCD 43, giving rise to an output in which the light and dark portions are averaged and there is little difference between signals generated at different light receiving points.

On the other hand, if the speed of the speckle pattern is lower than the scanning speed of the scanning sensor, the number of dark and light parts of the speckles 93' passing through the light receiving part of the CCD 43 will decrease, so a strong signal will be output from a point on the light receiving part of the CCD 43 through which more light speckle portions pass, and a weak signal will be output from a point through which more dark speckle portions pass. Therefore, by optimizing the scanning speed of the scanning sensor with respect to speckle patterns arising from objects moving at different speeds and obtaining the intensity ratio of signals output by the scanning sensor, it becomes possible to discriminate between objects traveling at different speeds.

If, as shown in FIG. 5, with respect to the blood vessel image formed on the CCD 43, the ratio between the image in a direction parallel to the blood vessel 16c and the image in a direction perpendicular to the blood vessel is altered to compress it in the direction parallel to the blood vessel. This enables the amount of incident light on the CCD 43 to be increased without degradation of resolution in the direction perpendicular to the blood vessel. There will be a slight degradation in the signal intensity ratio of the light and dark speckle portions, but as there will be a considerable decrease in the dark portions, there will be few discrimination errors.

FIGS. 13 to 20 relate to other embodiments which have the same object as the embodiment described above but are not based on the optical system of a fundus camera. In the descriptions, parts that are the same as parts in the above embodiment have been given the same reference numerals, and a detailed description of such parts is omitted.

Figure 14:
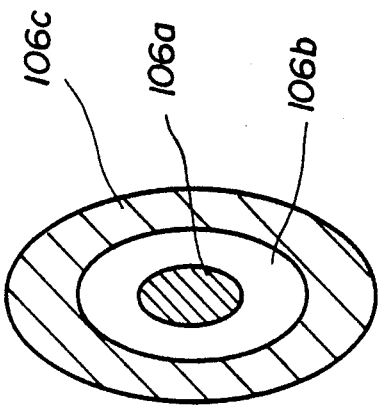
FIG. 14 shows details of a movable mirror.
Figure 13:
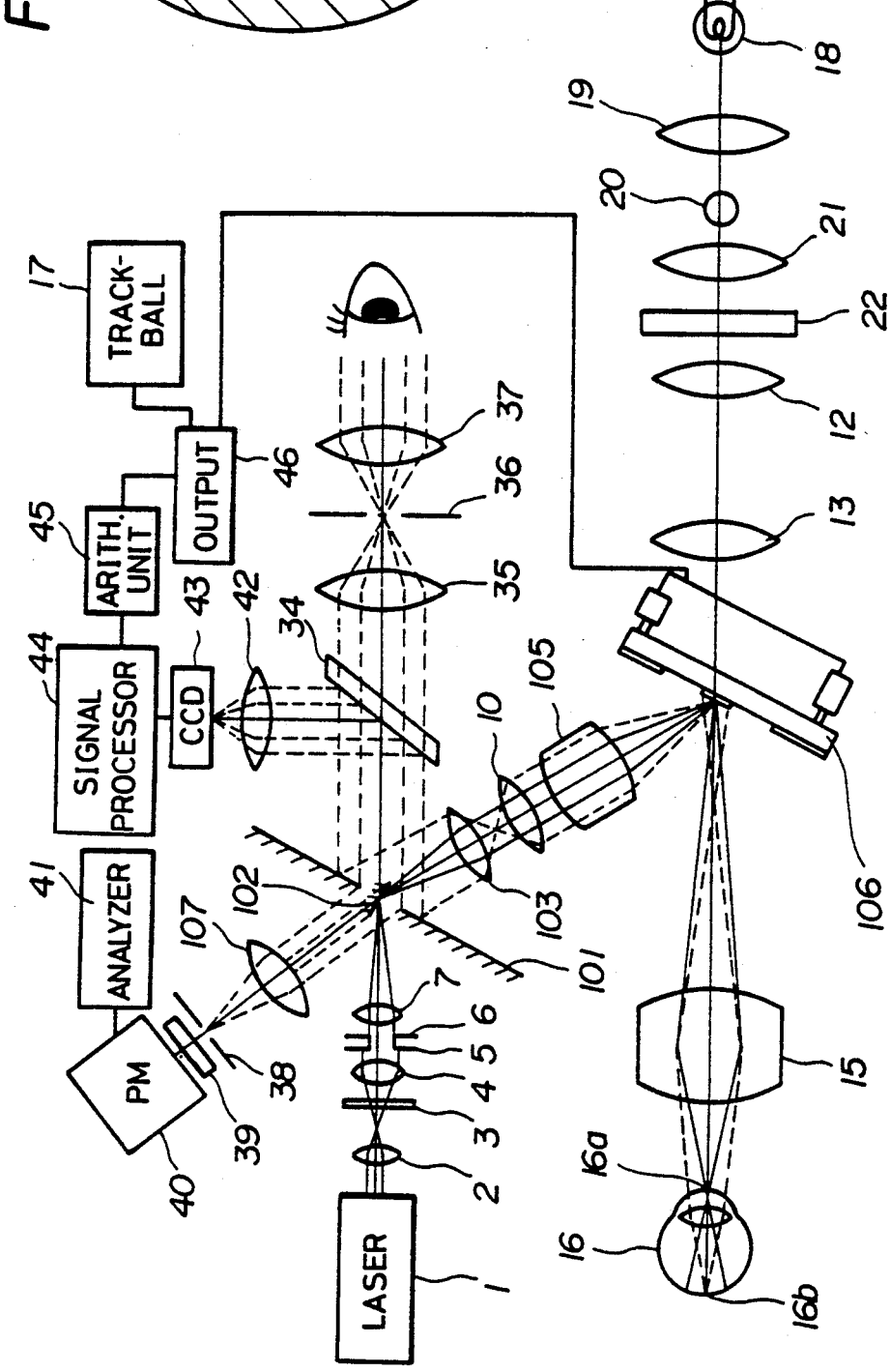
FIG. 13 is a schematic view of another embodiment of the apparatus of the invention.

With reference to FIG. 13, a laser beam is converged on a small mirror 102 located at a position that is a conjugate of the cornea 16a. The light passes through relay lenses 103 and 104 and a focusing lens 105, is reflected by a swingable mirror 106 located at a position that is a conjugate of the cornea 16a and is projected into the eye fundus 16b via the objective lens 15. As shown in FIG. 14, the swingable mirror 106 is constituted of a total reflection mirror 106a, a transparent section 106b and a portion 106c with a low reflectance that does not transmit light.

Part of the light which is scattered and reflected by the eye fundus 16b passes back along the same light path, is reflected by a ring mirror 101 and forms an image on the CCD 43. Light that is passed by the ring mirror 101 and the small mirror 102 is formed into an image at the pinhole aperture 38 by an imaging lens 107.

In the first embodiment the mirror used for beam alignment and tracking and the mirror used for observation-point alignment and tracking move independently, a drawback of which is that it complicates the alignment operation. In addition, during tracking the mirrors would sometimes move out of mutual alignment. To solve such problems, in this embodiment the function of the two mirrors have been integrated into a single mirror.

FIG. 15 is a schematic diagram of a signal processor comprised of a selector 67, memory 68, data latch 69, size comparator 70 and controller 71. The controller 71 controls the timing of memory 68 reads and writes. The preceding read from the memory 68 is latched by the data latch 69. A size comparison is made between the value of this data and the value of the preceding data converted to 8-bit digital form by the A/D converter 55. Data which in accordance with the decision of the size comparator 70 has a large value is selected by the selector 67 and written into the memory 68, the preceding data being erased in the process. This is carried out with respect to the values of all the signals output by the CCD 43. This is done a plurality of times and the 8-bit digital blood vessel discrimination signal is output to the arithmetic unit. This processing compensates for the dark parts of the speckle signals to provide a more faithful blood vessel discrimination signal.

Figure 17A:
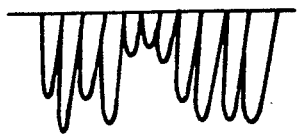
FIGS. 17a to 17d show waveforms of CCD output signals.
Figure 17B:
Figure 17C:
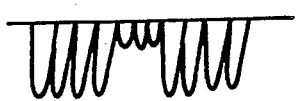

The same effect can be obtained with the signal processor arrangement shown in FIG. 16. In this arrangement two CCDs 43 and 43' are provided to receive eye fundus images. The outputs from the CCDs 43 and 43' are passed through corresponding high-pass filters 51, 51' and amplifiers 52, 52', resulting in the type of output signals shown in FIGS. 17a and 17b. The outputs of respective absolute value circuits are input to a size comparator 62, which selects and outputs the strongest of these input signals. FIG. 17c shows an output waveform of the size comparator 62.

Figure 17D:

Output signals from the size comparator 62 are input to the amplifier with limiter 54 where the required parts of the signals are amplified and the unnecessary parts suppressed by the limiter, thereby producing the signal waveforms shown in FIG. 17d and extracting blood vessel discrimination signals. This embodiment has been described with reference to the use of two CCDs, but the invention is not limited to two; the same effect can be obtained with a larger number. For the CCD 43 shown in FIG. 15, an area sensor may be used instead of a linear sensor and the same effect obtained by the addition of a linear sensor's multiple lines.

Figure 18:
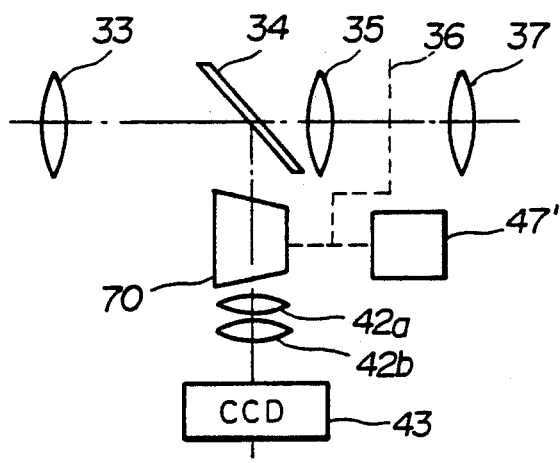
FIG. 18 shows the arrangement of an image rotator.

An image rotator 70 may be used to arrange the blood vessel image in perpendicularly to the CCD 43. With reference to FIG. 18, the blood vessel image formed on the face of the CCD 43 may be rotated instead. The image rotator is linked to the reticle 36 so that both rotate together. For angular data a potentiometer 47' is provided for detecting the angle of rotation of the image rotator.

Figure 19:
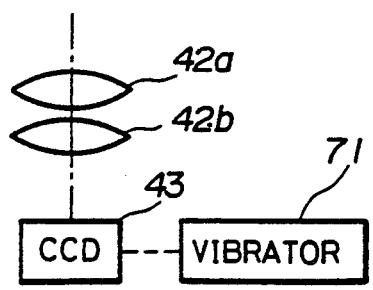
FIGS. 19 and 20 show an arrangement for oscillating an image on the CCD.
Figure 20:
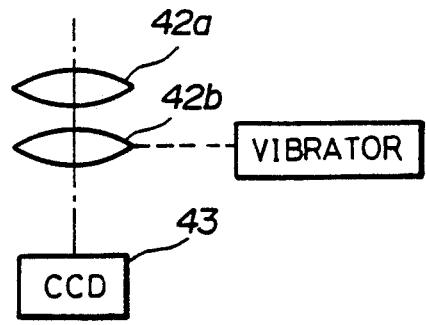

With reference to FIG. 19, the CCD 43 may be oscillated by a vibrator 71 at a low frequency and amplitude compared to the movement of speckles in the direction of the blood vessel the image of which is formed on the CCD. Alternatively, the vibrator 71 may be arranged so that it oscillates the lens 42b disposed in front of the CCD. Even with the use of oscillations having a low frequency and amplitude compared to the movement of speckles, the effect obtained will be the same as when the image is compressed in a direction parallel to the blood vessel.

When the CCD 43 is a linear sensor, no resolution is required in a direction parallel to the long axis of the blood vessel the image of which is produced by the laser speckle light. Therefore, the compression along the long axis of the blood vessel can be effected at the Fourier plane, but it must be effected at the image plane in the direction perpendicular to the blood vessel because it needs resolution.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention should not be limited to the particular embodiment disclosed as the best mode contemplated for carrying out the invention, but that the invention will include all embodiments falling within the scope of the appended claims.

What is claimed is:

1. An ophthalmological measurement method comprising the steps:
    projecting a laser beam having a predetermined diameter to an eye fundus;
    detecting motion of a laser speckle pattern formed by laser light scattered and reflected from the eye fundus at an observation point as fluctuations in the speckle light intensity;
    producing a speckle signal from the fluctuations in the speckle light intensity; and
    evaluating the speckle signal to derive its center of gravity, which is taken as a central position of a blood vessel in the eye fundus to identify a blood vessel part of the eye fundus.

2. An ophthalmological measurement method according to claim 1, further comprising the steps of detecting any movement of the identified blood vessel part of the eye fundus, and adjusting the position of the region illuminated by the laser beam and the position of the observation point by an amount corresponding to the amount of blood vessel movement to track the blood vessel part automatically.

3. An ophthalmological measurement method according to claim 2, wherein sets of data of the central position of the blood vessel are sampled, differences between consecutive sets of data are obtained to determined the amount of movement of the blood vessel image, and correction amounts for the automatic tracking are obtained from the amount of movement.

4. An ophthalmological measurement method according to claim 2, wherein the automatic tracking is implemented by moving the blood vessel image to be tracked to the speckle pattern observation point.

5. An ophthalmological measurement method according to claim 2, wherein the position of the region illuminated by the laser beam automatically tracks the center of the blood vessel to be tracked.

6. An ophthalmological measurement apparatus in which an eye fundus is illuminated by a laser beam having a predetermined diameter and motion of a laser speckle pattern formed by laser light scattered and reflected from the eye fundus is detected at an observation point as fluctuations in the speckle light intensity to produce a speckle signal which is evaluated for ophthalmological measurement, comprising: a laser for producing a laser beam;
    an optical system for projecting the laser beam to a region of the eye fundus including a blood vessel concerned;
    means for detecting movement of a laser speckle pattern formed by light scattered by the eye fundus as fluctuations in the light intensity of the speckles at an observation point; and
    means for processing a speckle signal obtained from the detecting means to derive therefrom a center of gravity;
    wherein the thus obtained center of gravity is taken as a center of a blood vessel to identify the blood vessel.

7. An ophthalmological measurement apparatus according to claim 6, further comprising means for detecting the amount of any movement a blood vessel part makes and means for automatically tracking the blood vessel part by adjusting the position of the region illuminated by the laser beam and the position of the observation point by an amount corresponding to the detected amount of blood vessel movement.

8. An ophthalmological measurement apparatus according to claim 7, further comprising a mechanism for deflecting the laser beam into alignment with the blood vessel to be tracked.

9. An ophthalmological measurement apparatus according to claim 8, wherein the mechanism includes a moveable mirror for deflecting the laser beam.

10. An ophthalmological measurement apparatus according to claim 7, further comprising a first mirror for deflecting the laser beam into the blood vessel for automatic tracking and a second mirror for defecting the blood vessel image into alignment with the observation point.

11. An ophthalmological measurement apparatus according to claim 10, wherein both the mirrors are integrated.

12. An ophthalmological measurement apparatus according to claim 6, wherein said means for detecting includes at least one scanning sensor provided at the observation point for detecting fluctuations in speckle light intensity.

13. An ophthalmological measurement apparatus according to claim 12, wherein there is a predetermined relationship between the size of a unit receiving area of the scanning sensor and size of the speckles.

14. An ophthalmological measurement apparatus according to claim 12, wherein there is a predetermined relationship between the scanning speed of the scanning sensor and the movement speed of the speckles.

15. An ophthalmological measurement apparatus according to claim 12, wherein said detecting means includes a plurality of scanning sensors and circuitry for selecting the output with the maximum value among the outputs of the sensors.

* * * * *